(12) United States Patent
Lin et al.

(10) Patent No.: US 7,744,741 B2
(45) Date of Patent: Jun. 29, 2010

(54) METHOD FOR DETERMINING EFFECTIVE DIFFUSIVITY OF SUBSTANCES THROUGH POROUS MATERIALS

(75) Inventors: Jing-Chie Lin, Tao-yuan (TW); Chien-Ming Lai, Tao-yuan (TW)

(73) Assignee: National Central University, Taoyuan (TW)

( * ) Notice: Subject to any disclaimer, the term of this patent is extended or adjusted under 35 U.S.C. 154(b) by 1063 days.

(21) Appl. No.: 11/284,811

(22) Filed: Nov. 23, 2005

(65) Prior Publication Data

US 2006/0254931 A1    Nov. 16, 2006

(30) Foreign Application Priority Data

May 13, 2005    (TW) .............................. 94115495 A

(51) Int. Cl.
*G01N 27/31*    (2006.01)

(52) U.S. Cl. .................... 205/787; 205/793; 429/145

(58) Field of Classification Search ............. 205/793, 205/787; 422/82, 82.01–82.02; 324/430; 429/145

See application file for complete search history.

(56) References Cited

U.S. PATENT DOCUMENTS

| 5,477,155 | A | * | 12/1995 | Proulx et al. | ............... | 324/71.1 |
| 5,624,538 | A | * | 4/1997 | Luft et al. | ................... | 204/418 |
| 2005/0179449 | A1 | * | 8/2005 | Wooton et al. | ............. | 324/691 |

OTHER PUBLICATIONS

Rocha, M. S.; Simoes-Moreira, J. R. A simple impedance method for determining ethanol and regular gasoline mixtures mass contnets, Fuel, 2005, vol. 84, pp. 447-452.*

* cited by examiner

*Primary Examiner*—Nam X Nguyen
*Assistant Examiner*—Gurpreet Kaur
(74) *Attorney, Agent, or Firm*—Jackson IPG PLLC

(57) ABSTRACT

The present invention provides a new method to obtain an effective diffusivity for a certain substance in solutions that diffuse through a porous material. The porous material initially separates two solutions that are different in concentration of the substance. The concentration gradient gives rise to diffusion through the porous material, The concentration change of the substance in the low-concentration compartment is detected through a measurement of the electrochemical impedance data. By means of the measurement, an effective diffusivity coefficient of the substance through the porous material is calculated.

9 Claims, 13 Drawing Sheets

METHOD FOR DETERMINING EFFECTIVE DIFFUSIVITY OF SUBSTANCES THROUGH POROUS MATERIALS

FIELD OF THE INVENTION

The present invention relates to a method for obtaining a diffusivity coefficient; in particularly, relates to obtaining an inference for an effective diffusivity coefficient of certain substances through porous materials by using an electrochemical impedance analyzer along with the diffusivity owing to a concentration gradient of the substance in solutions.

DESCRIPTION OF THE RELATED ARTS

A general porous material can be a molecule sieve, a mesoporous material, an activated carbon fiber, or a polymeric nano-porous material, which is usually applied in fields of isolation, purification, absorption, etc. When producing a porous material, the following factors are concerned, including the pore size, the uniformity of pore distribution, the surface characteristic (hydrophilicity or hydrophobicity), the porosity and the permeability coefficient, so that the characteristics of the porous material can be well controlled.

There are two major methods through which the characteristics of the porous material can be determined: one is BET (Brunauer, Emmett, and Teller) method and the other is mercury porosimetry. Both methods are briefly described as follows:

1. When the aperture of the porous material is in the range between 0.35 and 350 nm (nanometer), BET is usually used, which utilizes the absorption and the congealment of nitrogen to detect pore size, specific surface area of pore, pore structure, etc. and is a critical tool for the research on porous material.

2. The method of mercury porosimetry is generally used for the porous material whose pore aperture is greater than 3.6 μm (micrometer). By means of thrusting mercury into the pores of the specimen, the pore size, pore structure, specific surface area of the pores, pore structure, etc. can be determined. Recently, merchandised Ultra-high pressure mercury porosimetry analyzer has been developed to have the capability of determining the pore size of the porous material which comprises a diameter smaller than 3 nm.

In general, when using any one of the above methods, no matter it is BET or mercury porosimetry, the cost for the devices is expensive; and, for achieving the requirement of accuracy, the detection and the calculation take time. Moreover, when doing the detection with traditional devices, pore structure of the specimen is apt to be damaged, Therefore, these methods belong to destructive detections.

When using BET for detecting a porous material, very precise results may obtain. Yet, the experiment time is long; the calculation is complex and takes time; and, it can not be applied to a porous material which has pores with big aperture (>350 nm).

In the other hand, when mercury porosimetry analyzer is used, a major shortage can be that the mercury is poisonous and mercury waste is still a problem lack of a valid solution until now. Besides, because the surface tension of the mercury is very big and its figure do not easily deform with the surface changes of the shape of the solid pore, a great error may occur when detecting a specimen whose surface is specifically treated (e.g. through a hydrophilic process or a hydrophobic process).

Therefore, the prior arts do not fulfill users' requests on actual use.

SUMMARY OF THE INVENTION

Thus, the main purpose of the present invention is to obtain concentration changes of a solution where the solution is diffused through a porous material owing to a concentration gradient of the substance in the solution; and so as to obtain an inference for an effective diffusivity coefficient of the porous material by using an electrochemical impedance analyzer.

To achieve the above purpose, the present invention is a method for determining an effective diffusivity of a certain substance through porous materials, where a porous material is immersed in between a compartment loaded with a high-concentration solution and a compartment loaded with a low-concentration solution; a probe connecting to an electrochemical impedance analyzer is set in the compartment with the low-concentration solution; concentration changes of the low-concentration solution occur with a diffusivity between two ends of the porous material owing to a concentration gradient of the substance in the solutions; and data of the concentration changes are obtained by the probe and are transferred to the electrochemical impedance analyzer to obtain resistivity changes so as to acquire an inference for a diffusivity coefficient of the porous material. Accordingly, a novel method for determining an effective diffusivity of a certain substance through porous materials is obtained.

BRIEF DESCRIPTIONS OF THE DRAWINGS

The present invention will be better understood from the following detailed description of the preferred embodiment according to the present invention, taken in conjunction with the accompanying drawings, in which FIG. 1 is a view showing devices used according to the present invention;

Figure 12:
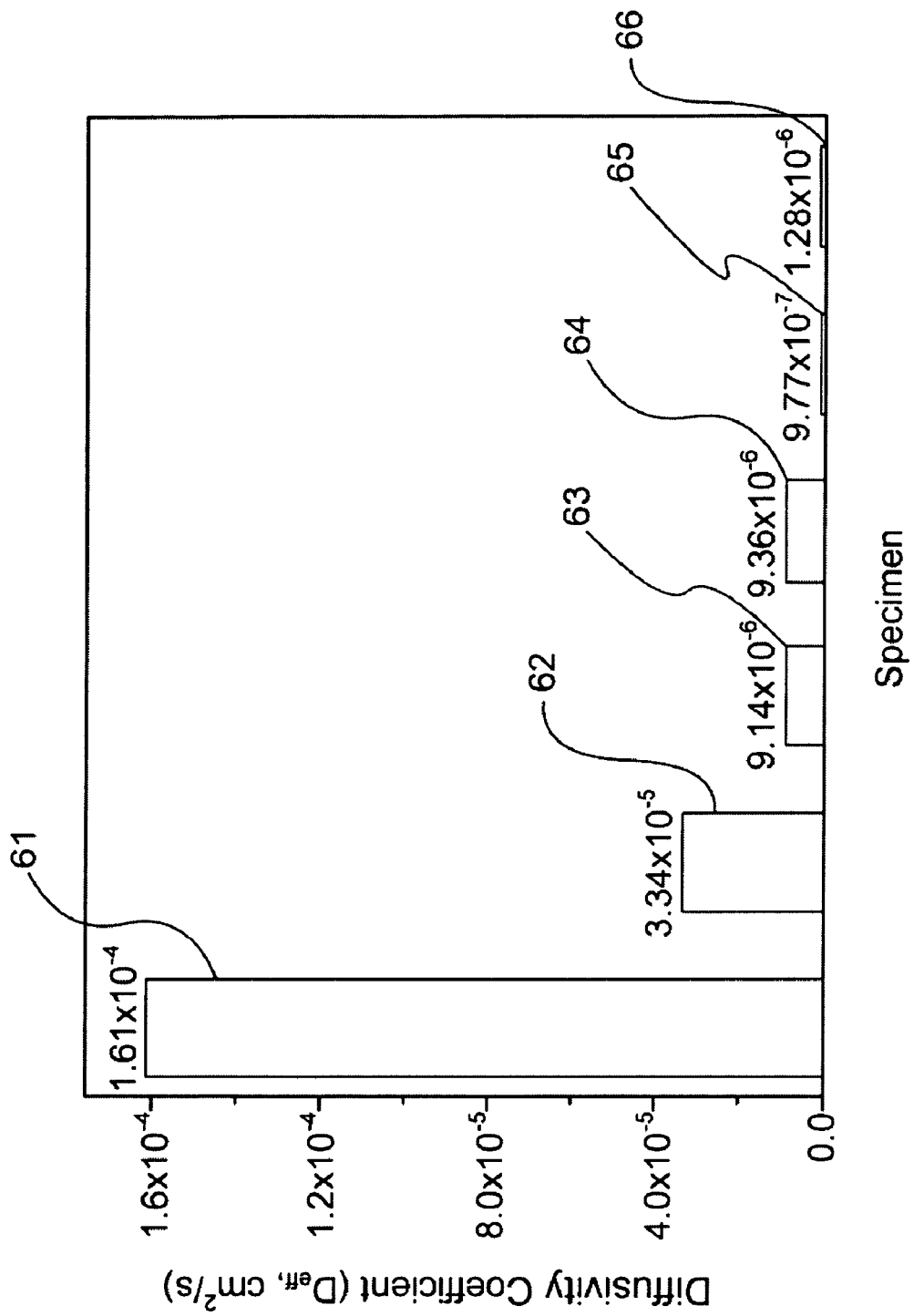
Figure 13:
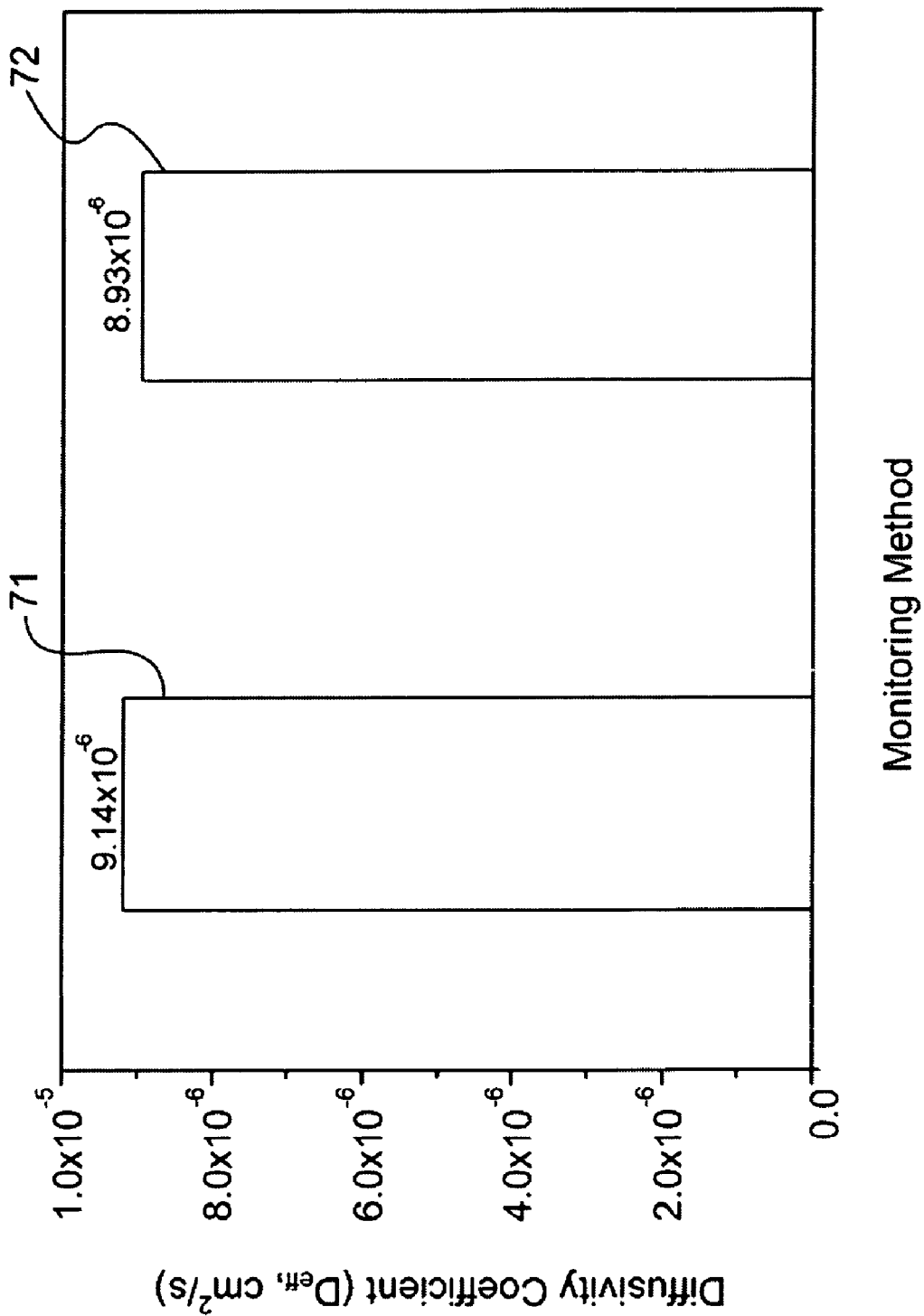

FIG. 12 is a view showing average methanol effective diffusivity coefficients of various porous materials for testing according to the present invention; and FIG. 13 is a view showing a comparison between the effective diffusivity coefficients obtained through the detecting method according to the present invention and the effective diffusivity coefficients obtained through GC (gas chromatography) concentration measurement.

DESCRIPTION OF THE PREFERRED EMBODIMENT

The following description of the preferred embodiment is provided to understand the features and the structures of the present invention.

Figure 1:
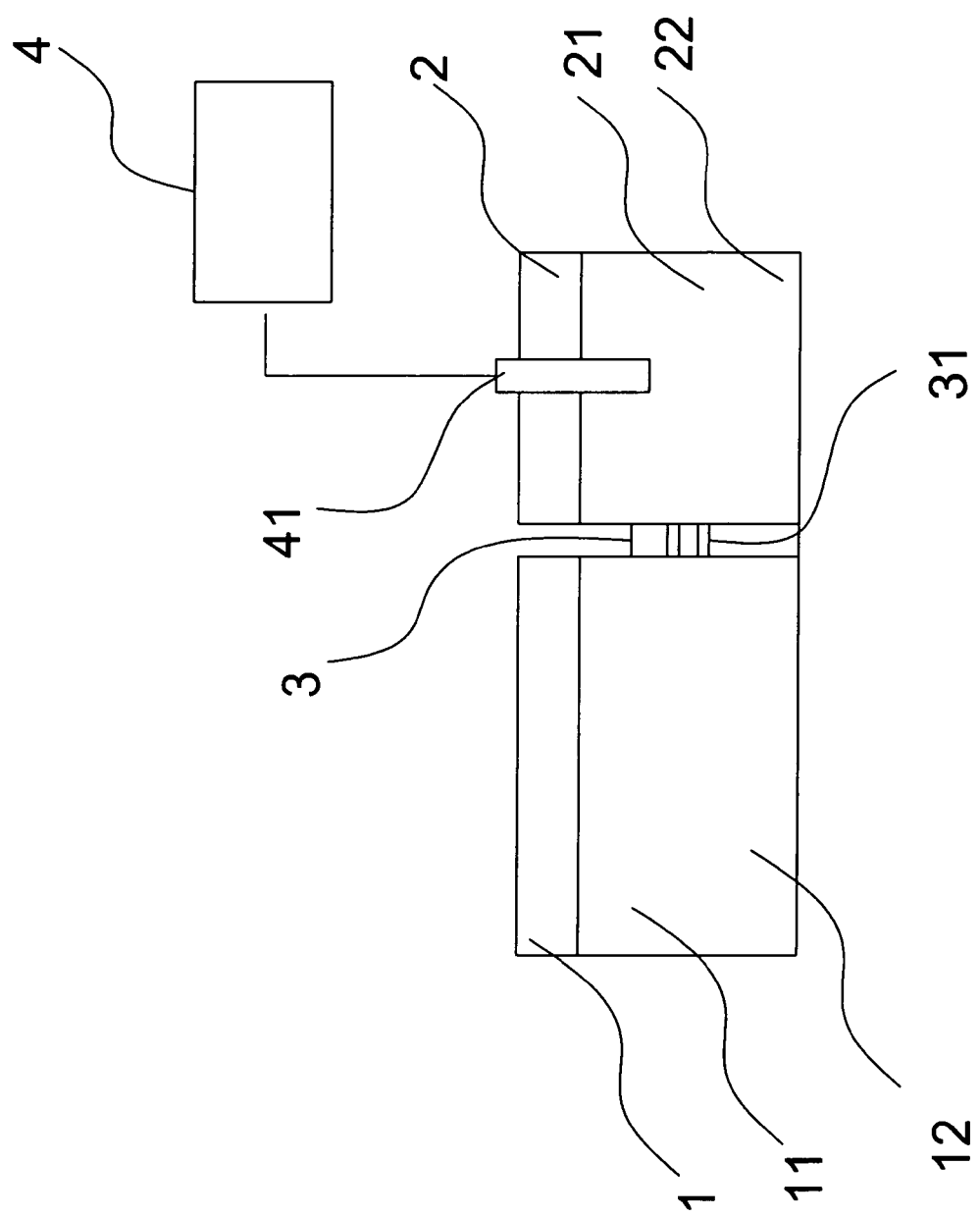
Figure 2:
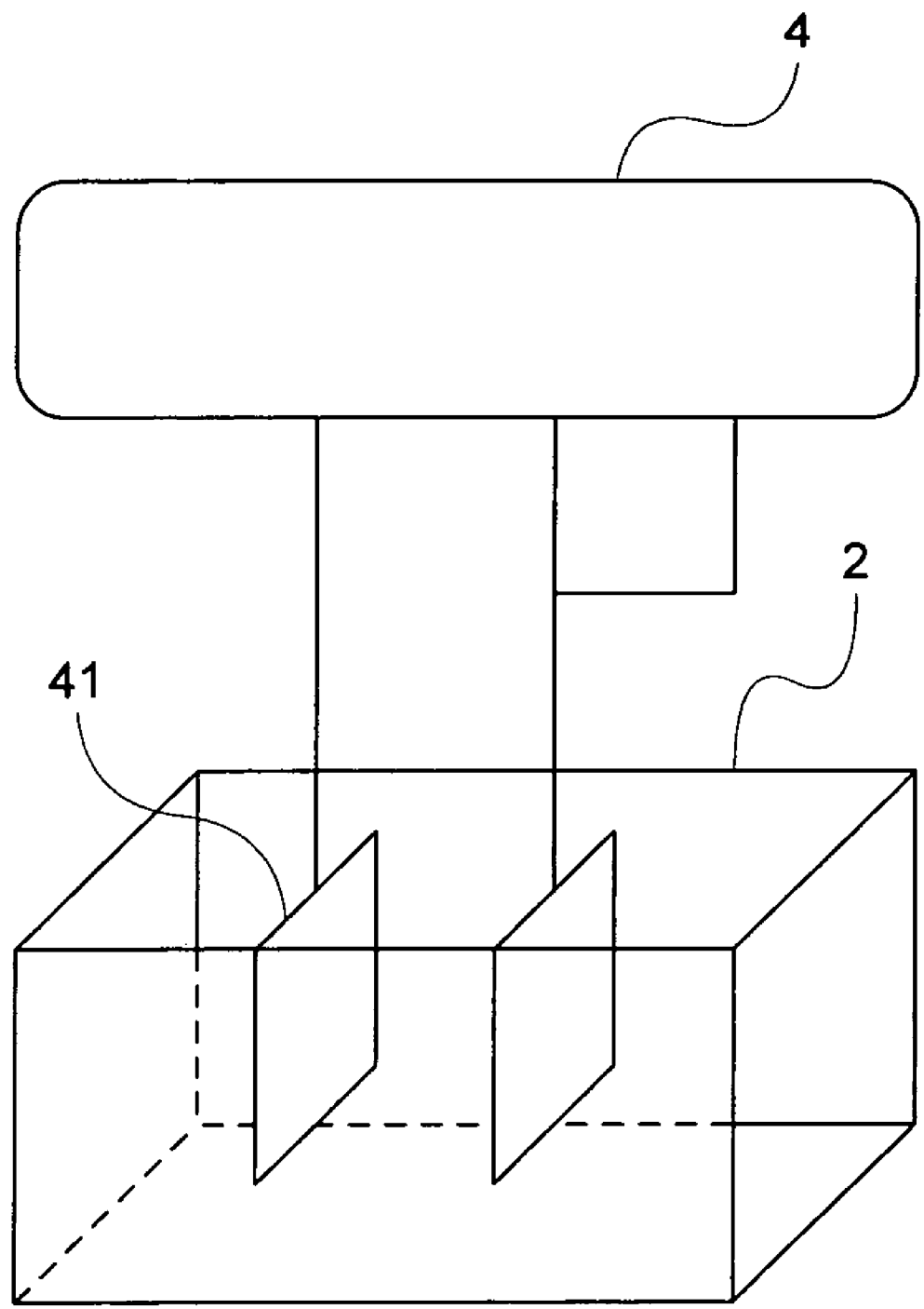
FIG. 2 is a view showing a connection between an electrochemical impedance analyzer and a probe according to the present invention.

Please refer to FIG. 1 and FIG. 2, which are views showing devices used and a connection between an electrochemical impedance analyzer and a probe, according to the present invention. As shown in the figures, the present invention is a method for determining an effective diffusivity of a certain substance through porous materials, which comprises the following steps:

(a) A first compartment [1] and a second compartment [2] are obtained. Both compartments [1,2] are loaded with a high-permeable solution [11,21], which is methanol or ethanol added with a conductive solution [12,22]. Therein, the high-permeable solution [11,21] comprises a concentration between 0 M (molar, mole per liter) and 20 M; and the permeable solution [11] in the first compartment [1] comprises a first concentration higher than a second concentration of the permeable solution [21] in the second compartment [2]. In addition, the conductive solution [12,22] is a solution added with a salt, an acidity or an alkalinity; and comprises a concentration between 0.1 M and 2 M.

(b) A material [3] is obtained, which is a porous material went through a hydrophilic process or a hydrophobic process having an aperture for every pore [31] between 1 nm and 100 μm. The material [3] is then immersed in between the first compartment [1] and the second compartment [2] to obtain a concentration gradient of the permeable solution between two ends of every pore [31]. As a result, the permeable solution [11] having the first concentration is diffused to the second compartment owing to the concentration gradient.

(c) A probe [41] is set in the second compartment [2] and is connected to an electrochemical impedance analyzer [4].

(d) And, concentration changes are happened to the permeable solution [21] having the second concentration owing to the diffusing of the permeable solution [11] having the first concentration. The concentration changes is detected by the probe [41] and the data of the concentration changes is transferred to the electrochemical impedance analyzer [4] to obtain resistivity changes of the permeable solution [21] in the second compartment [2], so that an effective diffusivity coefficient of the material [3] is figured out.

With the above steps, a novel method for determining an effective diffusivity of a certain substance through porous materials is obtained.

Figure 3:
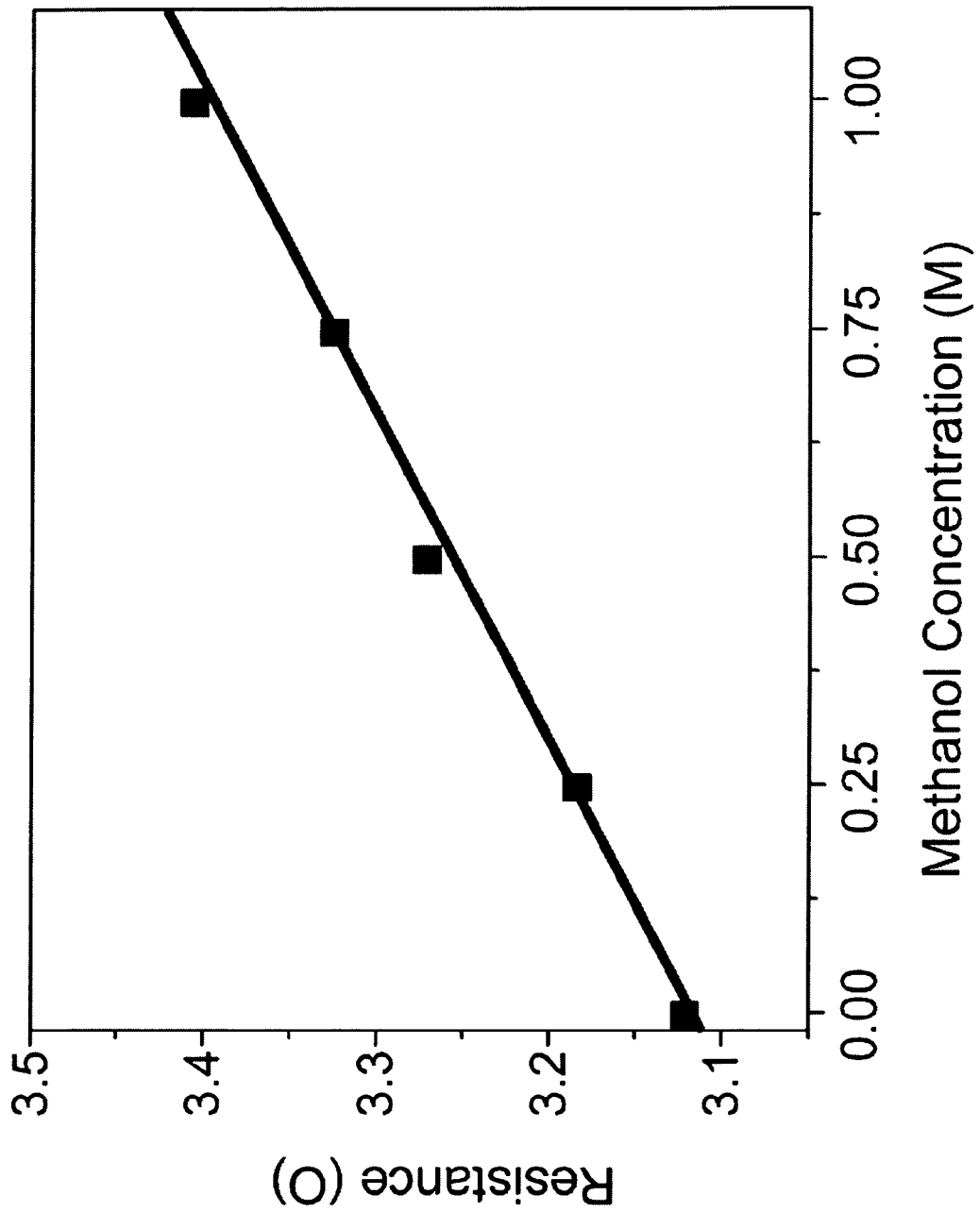
FIG. 3 is a view showing a relation between methanol concentrations and resistances under a temperature of 12.5° C. (Celsius) according to the present invention.
Figure 4:
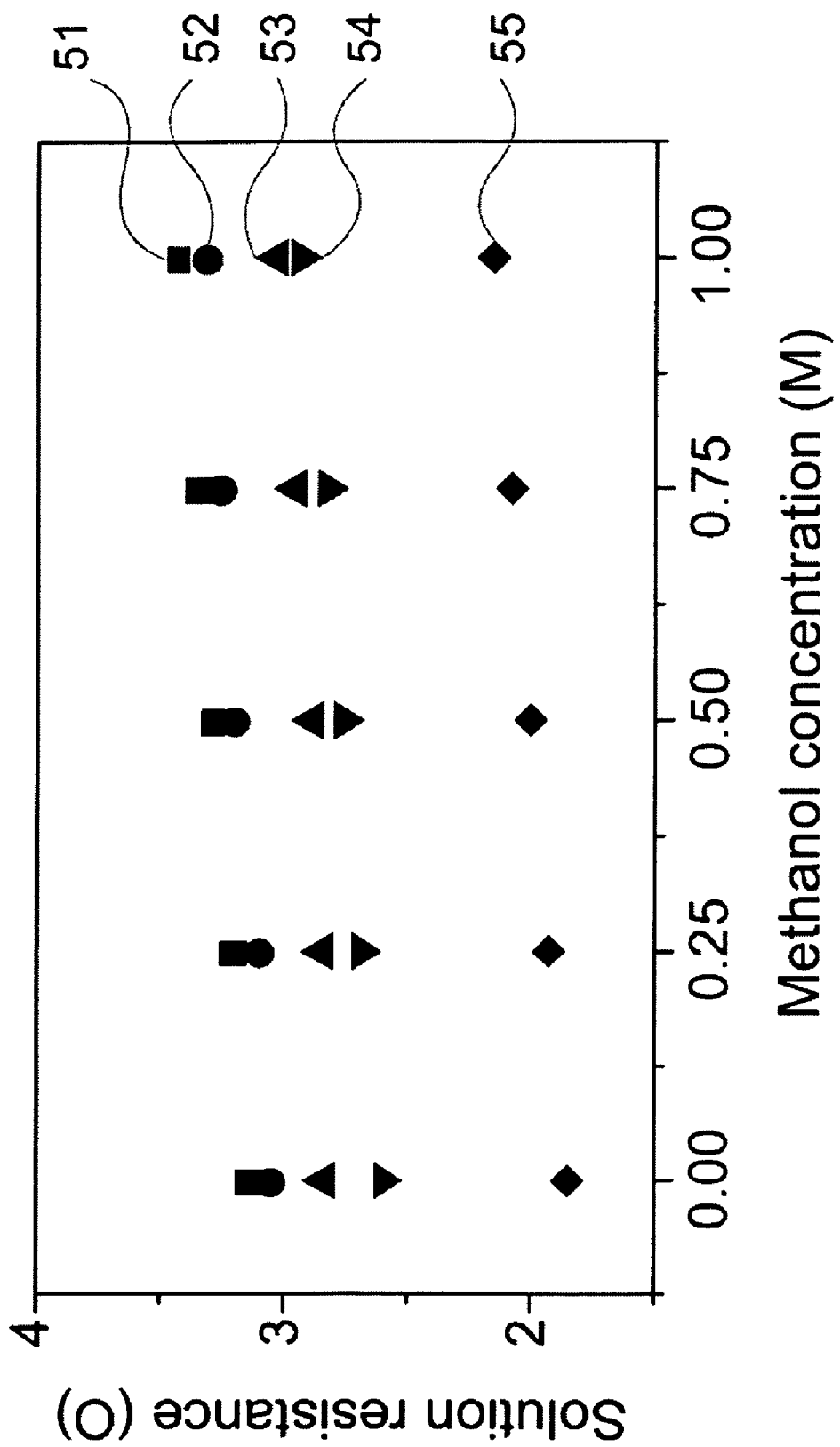
FIG. 4 is a view showing relations between methanol concentrations and resistances under various temperatures according to the present invention.

Please further refer to FIG. 3 and FIG. 4, which are views showing relations between methanol concentrations and resistances under a temperature of 12.5° C. and under various temperatures, according to the present invention. For obtaining data shown in the figures, experiments are taken. At an end of the material for testing [3] is a 500 ml (milliliter) high-concentration solution of 10 M methanol added with 0.5 M sulfuric acid; and at the other end of the material for testing [3] is a 100 ml low-concentration solution of 0 M methanol (i.e. no methanol) added with 0.5 M sulfuric acid. The probe [41] is made of two platinum flakes which expose 1 cm$^2$ (centimeter square) of surface area in the low-concentration solution for each and comprise a separation of 1 cm in between.

When measurements are taken under the above conditions, the electrochemical impedance analyzer [4] outputs AC (alternating current) signals, which in general are sine-wave signals of 10 mV (millivoltage), to the solution to detect a phase lead or a phase lag of the signals (i.e. the current) to obtain impedance signals. With the signal data obtained to be processed through an equivalent circuit simulation, a thorough understanding to the electrochemistry reactions is acquired. This is the impedance analysis done by the electrochemical impedance analyzer [4]. Thus, useful information are obtained from the measurements and are divided into three parts according to the frequencies of the signals: the solution resistances shown in the areas of high frequency, the electric double layer impedances shown in the areas of middle frequency and low frequency, and the mass transport impedances shown in the areas of extra-low frequency.

The electrochemical impedance analyzer [4] detects an infinitesimal diffusion in the pores [31] of the material for testing [3] through electrochemical impedance spectroscopy. An inference for infinitesimal concentration changes is obtained with the infinitesimal changes shown in the high-frequency area (representing the solution resistance) of the spectrum due to the diffusing of the high-concentration solution [11] to the low-concentration solution [21]. Based on an unsteady-state diffusivity equation (Fick's Law), an inference for effective diffusivity coefficients for the materials for testing [3] is obtained by using a commercial software 'MatLab'.

As shown in FIG. 3, under a temperature of 12.5° C., resistances for solutions with various concentrations of methanol are obtained; and, through linear regression, a linear equation for methanol concentration and resistance under 12.5° C. is obtained as R=3.1192+0.2844 C, where R is the resistance and C is the methanol concentration. As shown in FIG. 4, resistances for solutions under various temperatures having various concentrations of methanol are obtained. Thus, linear equations for methanol concentrations and resistances under various temperatures are obtained through linear regression with the data of the above resistances. Those linear equations are as follows: under 12.5° C. [51], R=3.1192+0.2844 C; under 20° C. [52], R=3.0408+0.2706 C; under 30° C. [53], R=2.8302+0.1817 C; under 40° C. [54], R=2.6073+0.3258 C; and, under 80° C. [55], R=1.8514+0.3053 C.

Figure 5:
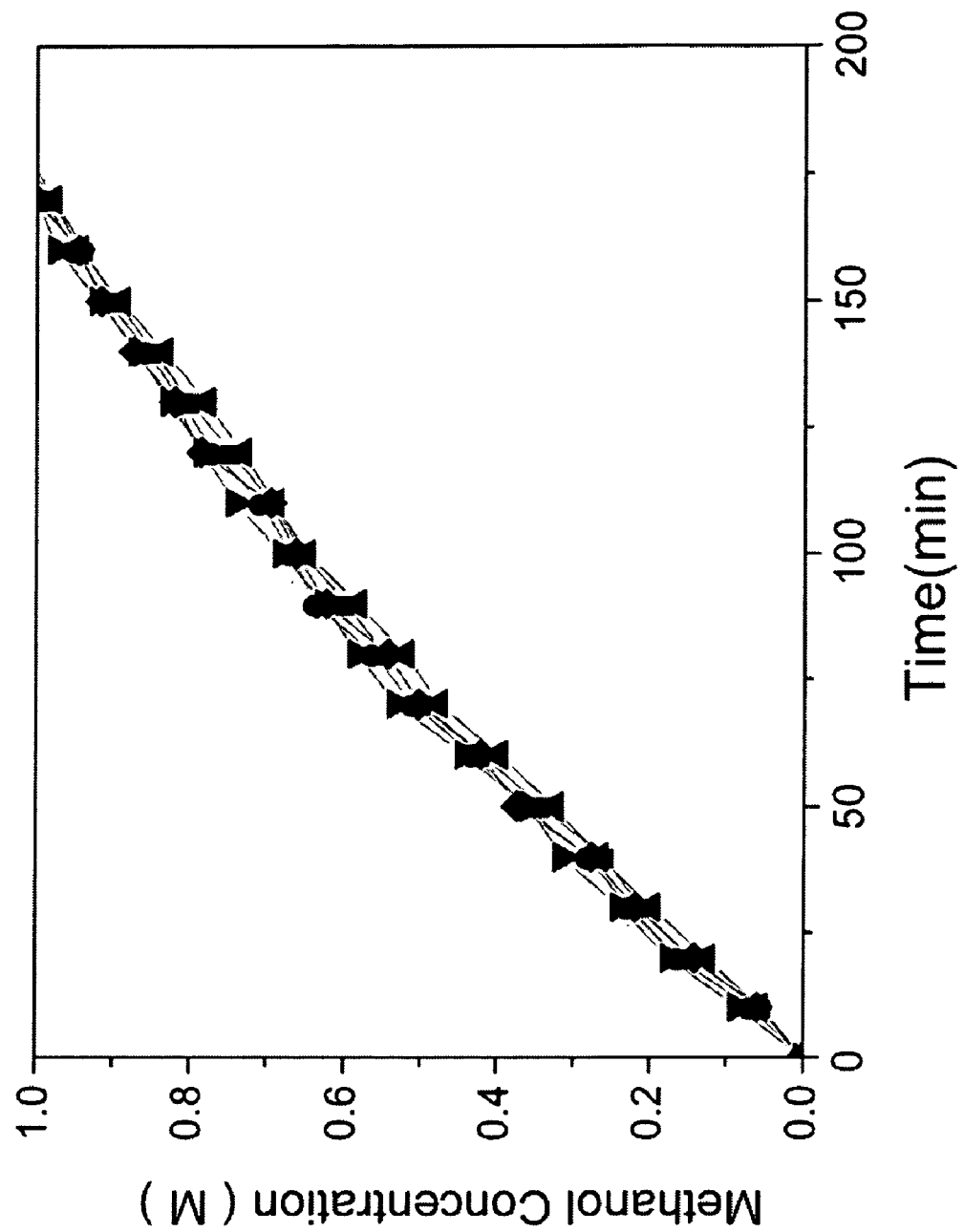
FIG. 5 is a view showing relations between methanol concentrations and time for a porous carbon fiber went through a hydrophobic process according to the present invention.

Please refer to FIG. 5, which is a view showing relations between methanol concentrations and time for a porous carbon fiber went through a hydrophobic process according to the present invention. For obtaining data shown in the figure, porous carbon fibers go through a hydrophobic process with 30% PTFE (Polytetrafluoroethylene, Teflon) and is coated with a 30 μm microporous layer so that fibers of SGL 31-EC are obtained. An end of the SGL 31-EC fiber is immersed in a high-concentration solution of 10 M methanol added with 0.5 M sulfuric acid; and the other end of the fiber is immersed in a low-concentration solution of 0 M methanol (no methanol) added with 0.5 M sulfuric acid. Changes of methanol concentration to time in the low-concentration solution are detected throughout five times of experiments. In the end, by using Matlab, an average effective diffusivity coefficient for SGL 31-EC is obtained as 8.05×10−6 cm2/s whose standard deviation is 1.45×10$^{-7}$ cm$^2$/S with a precision error below 2% (1.8%).

Please refer to FIG. 6 through FIG. 11, which are views showing relations between methanol concentrations and time for porous carbon fibers went through various hydrophobic processes according to the present invention. An experimental environment according to the present invention for obtaining the above figures comprises a material for testing. An end, a first end, of the material for testing is immersed in a high-concentration solution of 10 M methanol added with 0.5 M sulfuric acid; and the other end, a second end, is immersed in a low-concentration solution of 0 M methanol added with 0.5 M sulfuric acid. For obtaining data shown in FIG. 6, five pieces of a porous carbon fiber (SGL 31-AA) are provided to be deposed in the experimental environment as materials for testing while changes of methanol concentration to time are detected at the second end; for obtaining data shown in FIG. 7, two pieces of a porous carbon fiber went through a hydrophobic process with 5% PTFE (SGL 31-BA) are provided; for FIG. 8, two pieces of a porous carbon fiber went through a hydrophobic process with 5% PTFE and coated with a 30 μm microporous layer (SGL 31-BC); for FIG. 9, two pieces of a porous carbon fiber went through a hydrophobic process with 30% PTFE and coated with a 30 μm microporous layer (SGL 31-EC); for FIG. 10, three pieces of a polymeric nano-porous material (Nafion 112); and, for FIG. 11, three pieces of another polymeric nano-porous material (Nafion 117).

Figure 6:
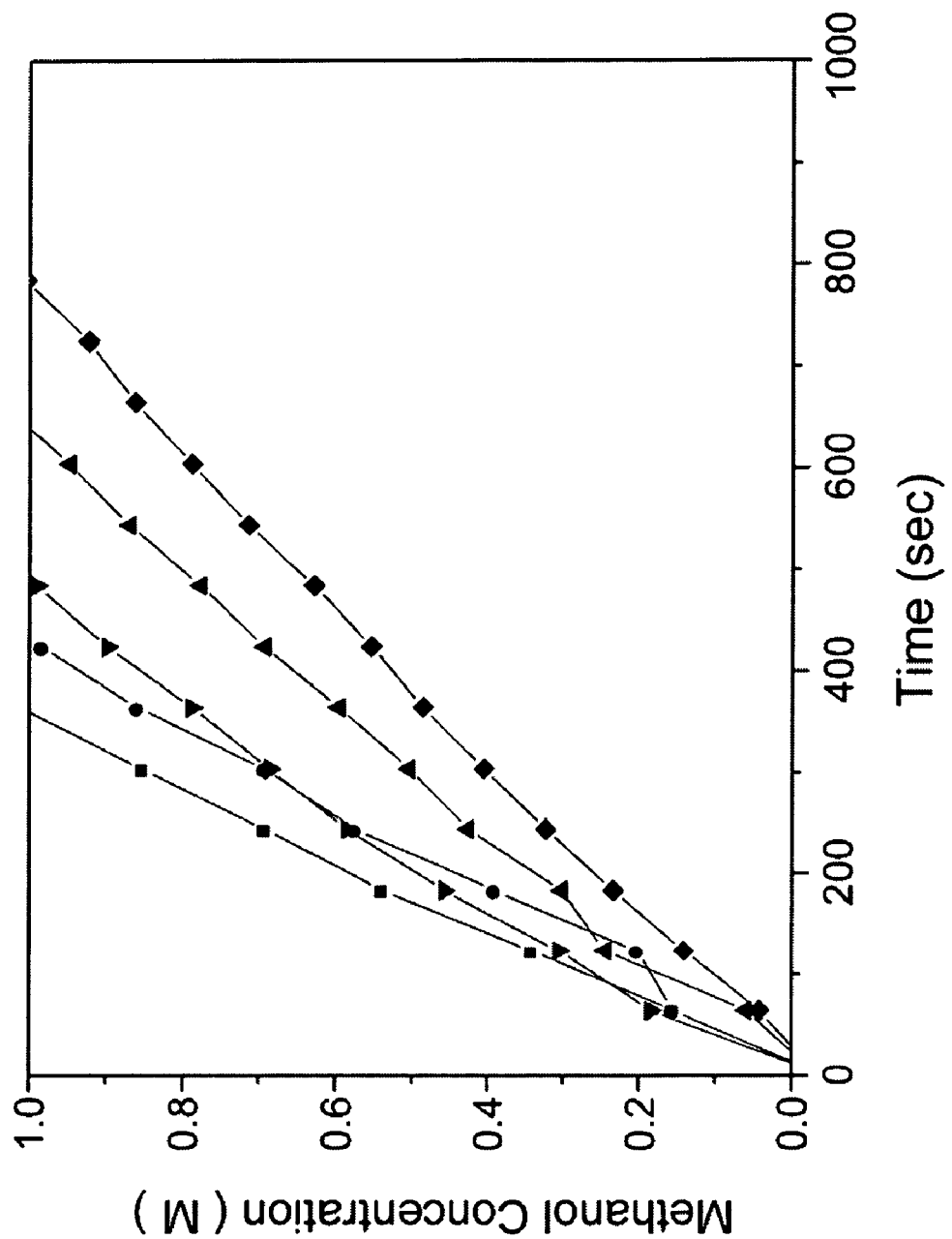
FIG. 6 through FIG. 11 are views showing relations between methanol concentrations and time for porous carbon fibers went through various hydrophobic processes according to the present invention.
Figure 7:
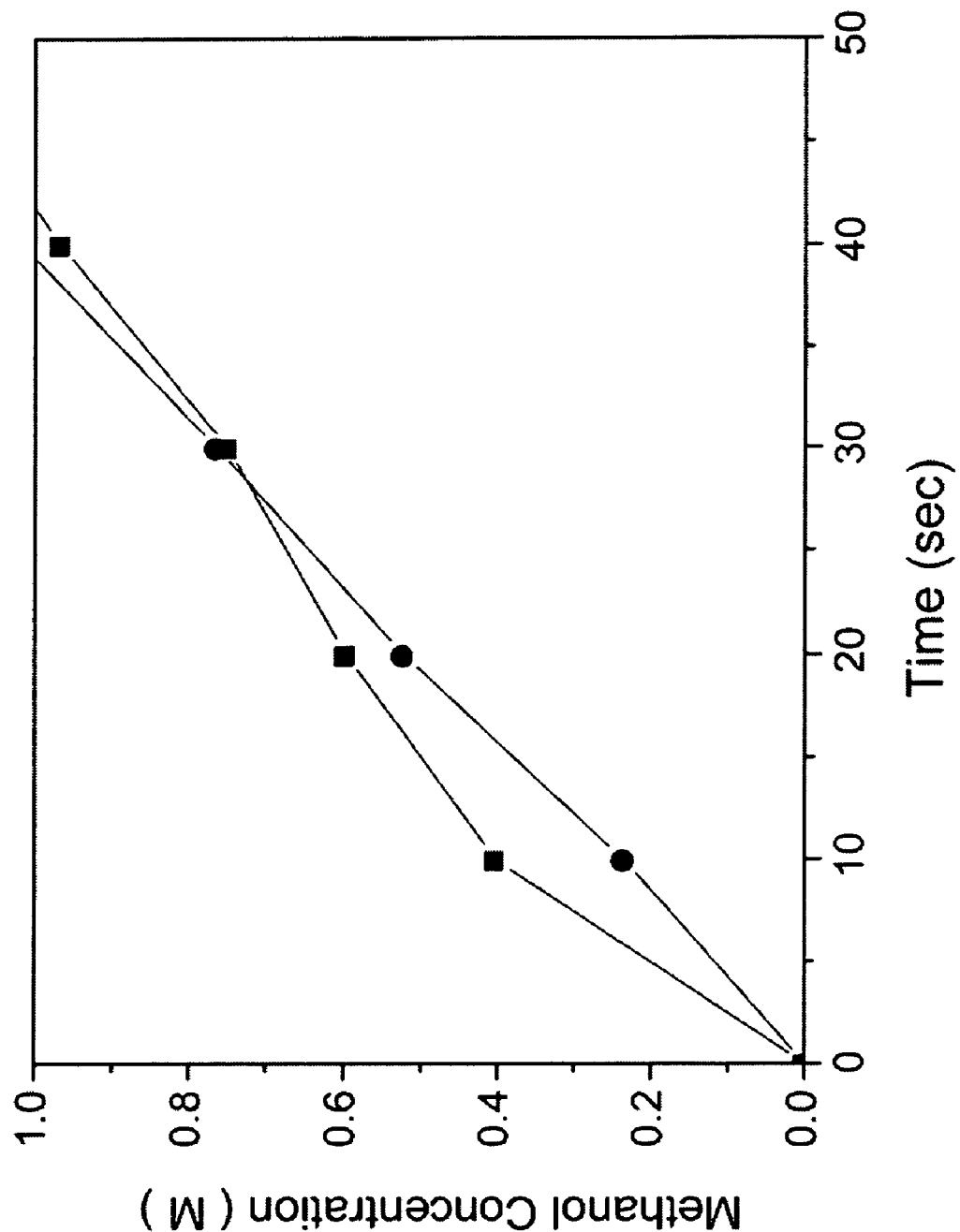
Figure 8:
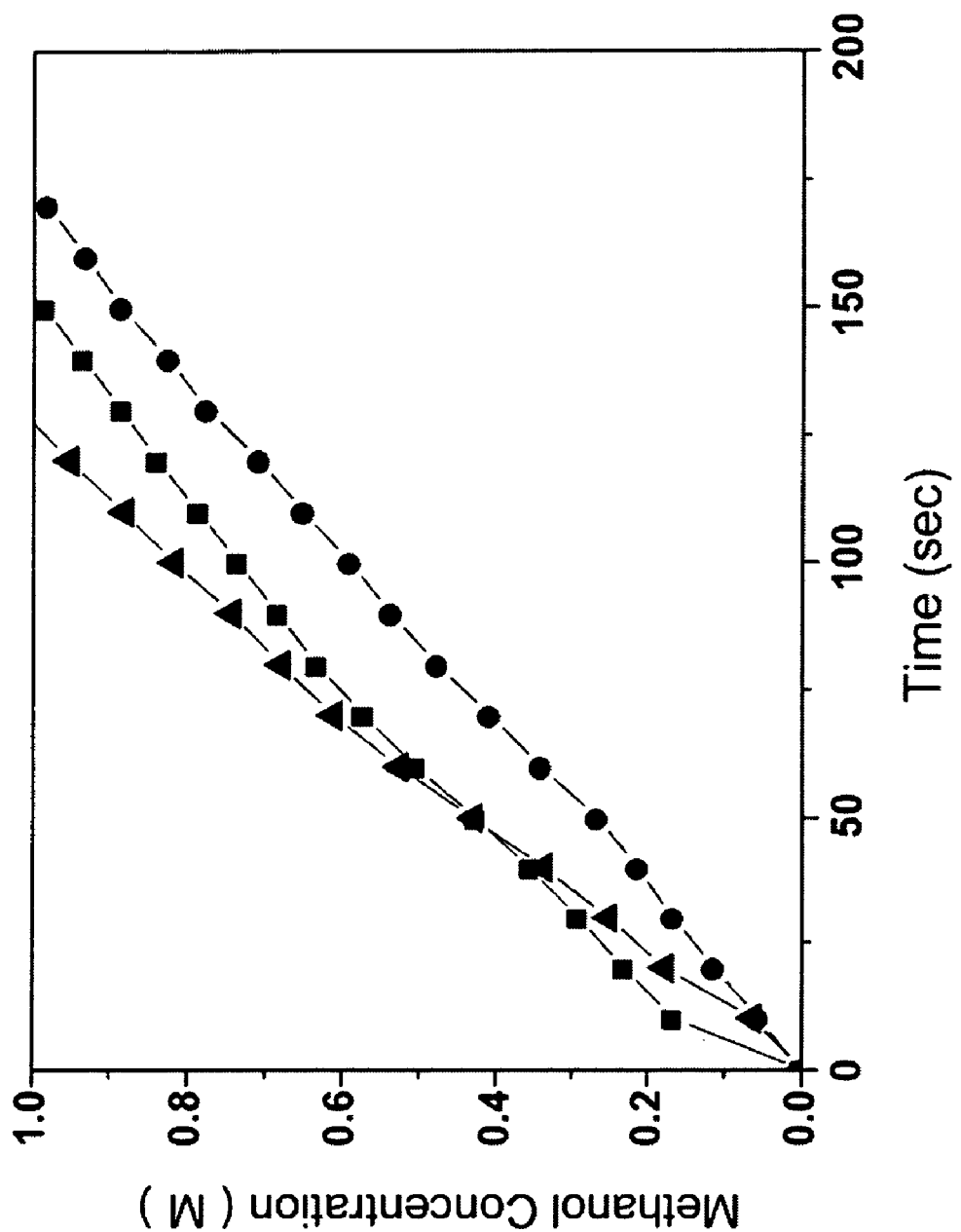
Figure 9:
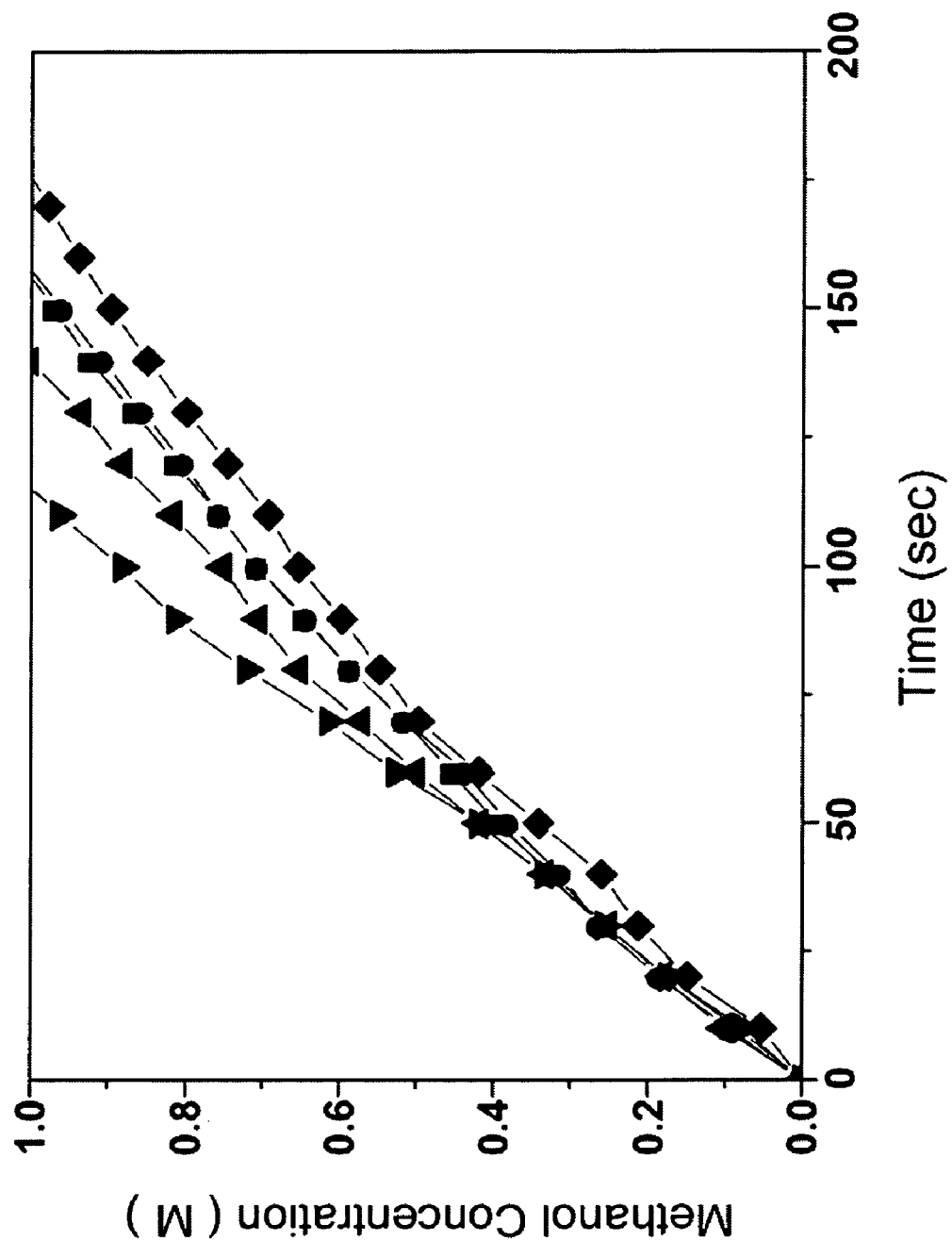
Figure 10:
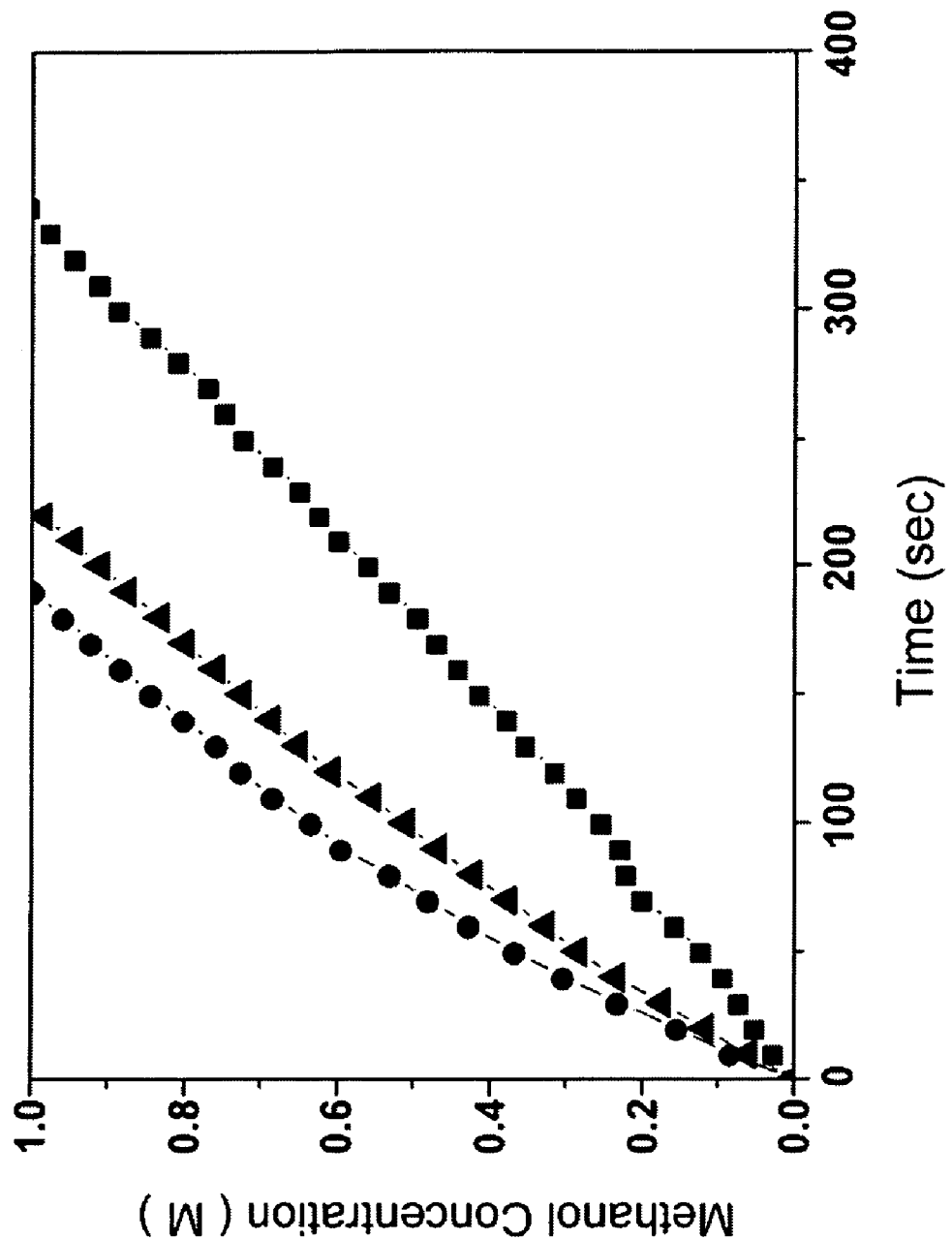
Figure 11:
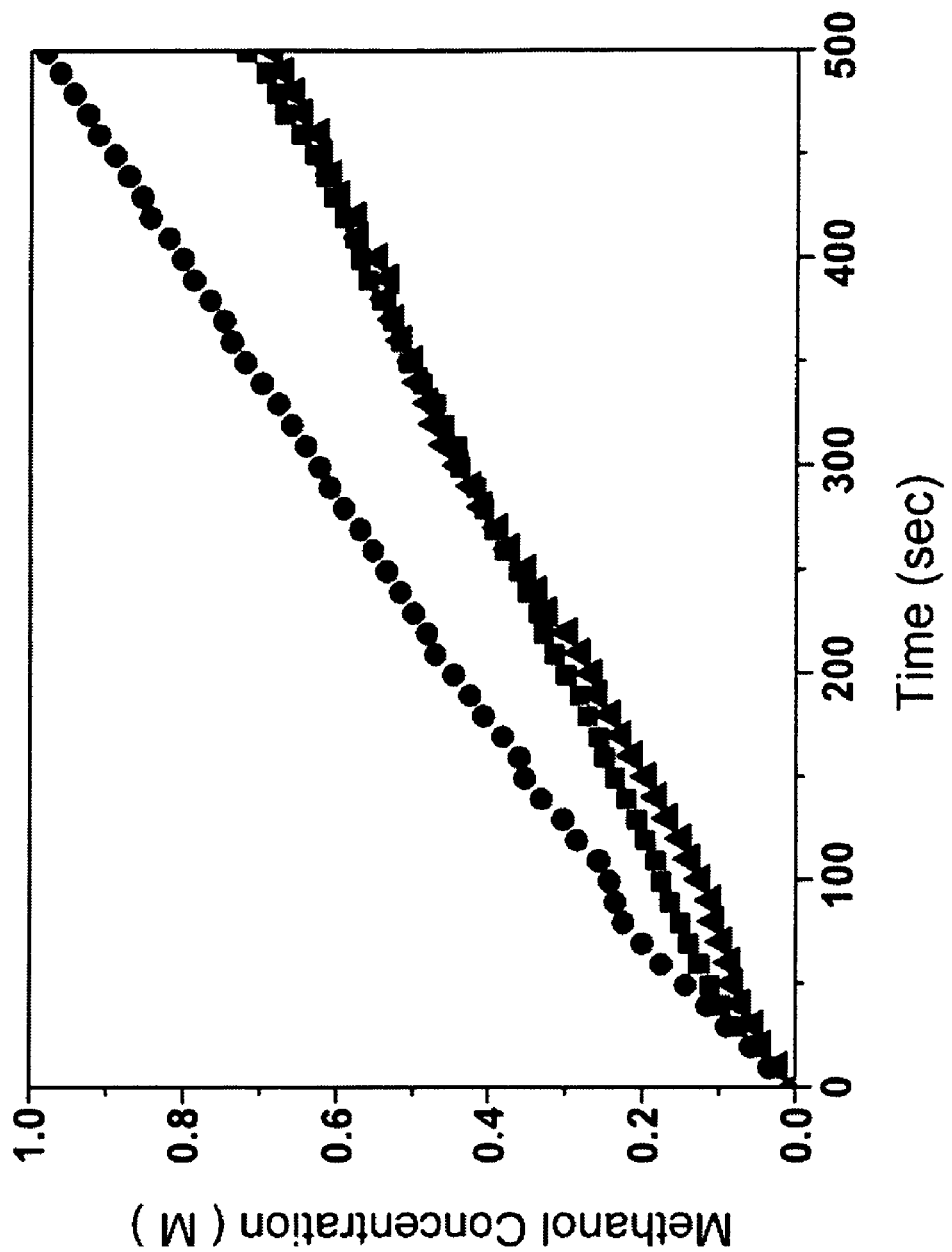

Please refer to FIG. 12, which is a view showing average methanol effective diffusivity coefficients of various porous materials for testing according to the present invention. As shown in the figure, average methanol effective diffusivity coefficients for various porous materials used in FIG. 6 through FIG. 11 are obtained by using Matlab with the data in shown in the figures, where the average methanol effective diffusivity coefficient for the porous material used in FIG. 6 is $1.61 \times 10^{-4}$ cm$^2$/s; for the porous material used in FIG. 7, $3.34 \times 10^{-5}$ cm$^2$/s; in FIG. 8, $9.14 \times 10^{-6}$ cm$^2$/s; in FIG. 9, $9.36 \times 10^{-6}$ cm$^2$/s; in FIG. 10, $9.77 \times 10^{-7}$ cm$^2$/s; and, in FIG. 11, $1.28 \times 10^{-6}$ cm$^2$/s.

Please refer to FIG. 13, which is a view showing a comparison between the effective diffusivity coefficients obtained through the detecting method of the present invention and the effective diffusivity coefficients obtained through GC concentration measurement. As shown in the figure, two effective diffusivity coefficients of the same SGL 31-BC specimen are obtained: one of $9.14 \times 10^{-6}$ cm$^2$/s is obtained through the detecting method of the present invention [71] and the other one of $8.93 \times 10^{-6}$ cm$^2$/s is obtained through the GC concentration measurement [72]. By comparing the two effective diffusivity coefficients, a precision error below 2.5% (2.35%) is obtained.

To sum up, the present invention is a method for determining an effective diffusivity of a certain substance through porous materials, where resistance of a solution is monitored with an electrochemical impedance analyzer to first obtain concentration changes owing to a concentration gradient of the substance in solutions causing the diffusing of the solution through the porous material and then to obtain an inference for an effective diffusivity coefficient of the porous material.

The preferred embodiment herein disclosed is not intended to limit the scope of the invention unnecessarily. Therefore, simple modifications or variations belonging to the equivalent of the scope of the claims and the instructions disclosed herein for a patent are all within the scope of the present invention.

What claimed is:

1. A method for determining an effective diffusivity of a known substance through porous materials, comprising the steps of:

(a) obtaining a first compartment loaded with a permeable solution having a first concentration, and obtaining a second compartment loaded with said permeable solution having a second concentration lower than said first concentration, said permeable solution mixed with a conductive solution;

(b) immersing said porous material in between said first compartment and said second compartment to obtain a concentration gradient of said permeable solution between two ends of each pore of said porous material to diffuse said permeable solution having said first concentration to said second compartment;

(c) setting a probe in said second compartment, said probe connecting to an electrochemical impedance analyzer; and (d) detecting data signals from the electrochemical impedance analyzer to obtain resistivity at various temperatures and for various times;

using an empirical formula based on a linear relationship of resistivity and concentration and Fick's law so as to obtain a value for an effective diffusivity coefficient of said porous material.

2. The method according to claim 1, wherein said permeable solution is selected from a group consisting of methanol and ethanol.

3. The method according to claim 1, wherein said conductive solution comprises a component selected from a group consisting of a salt, an acid, and a base.

4. The method according to claim 1 wherein said first concentration and said second concentration are in a range between OM (molar, mole per liter) and 20 M.

5. The method according to claim 1, wherein said conductive solution comprises a concentration between 0.1 M and 2 M.

6. The method according to claim 1 wherein each said pore comprises an aperture between 1 nm (nanometer) and 100 μm (micrometer).

7. The method according to claim 1, wherein said porous material is a porous material that has gone through a process selected from a group consisting of a hydrophilic process and a hydrophobic process.

8. The method according to claim 1, wherein said detecting is performed under a temperature between 10° C. and 80° C.

9. The method according to claim 1, wherein said method is a non-destructive method in which none of said solution is consumed and no reactant is generated.

* * * * *